(12) United States Patent
Nitzan

(10) Patent No.: US 12,059,379 B2
(45) Date of Patent: Aug. 13, 2024

(54) PREMATURE INFANT CARE SYSTEM

(71) Applicant: SHAARE ZEDEK SCIENTIFIC LTD., Jerusalem (IL)

(72) Inventor: Itamar Nitzan, Mevaseret Zion (IL)

(73) Assignee: SHAARE ZEDEK SCIENTIFIC LTD., Jerusalem (IL)

( * ) Notice: Subject to any disclaimer, the term of this patent is extended or adjusted under 35 U.S.C. 154(b) by 0 days.

(21) Appl. No.: 18/029,958

(22) PCT Filed: Oct. 10, 2021

(86) PCT No.: PCT/IL2021/051211
§ 371 (c)(1),
(2) Date: Apr. 3, 2023

(87) PCT Pub. No.: WO2022/074660
PCT Pub. Date: Apr. 14, 2022

(65) Prior Publication Data
US 2023/0363967 A1    Nov. 16, 2023

(30) Foreign Application Priority Data

Oct. 11, 2020   (GB) ..................... 2016124

(51) Int. Cl.
*A61G 11/00*   (2006.01)
*A61M 16/06*   (2006.01)
*A61M 16/10*   (2006.01)

(52) U.S. Cl.
CPC ....... *A61G 11/009* (2013.01); *A61M 16/1045* (2013.01); *A61B 2503/045* (2013.01);
(Continued)

(58) Field of Classification Search
CPC .... A61G 11/00; A61G 11/005; A61G 11/009; A61G 10/005; A61G 10/04;
(Continued)

(56) References Cited

U.S. PATENT DOCUMENTS 6,367,476 B1 * 4/2002 Conn ..................... A61G 10/04
135/121
10,390,630 B2   8/2019 Bucher
(Continued)

FOREIGN PATENT DOCUMENTS

DE         20114157 U1   2/2002

OTHER PUBLICATIONS

Zaylaa AJ, Rashid M, Shaib M, El Majzoub I. A Handy Preterm Infant Incubator for Providing Intensive Care: Simulation, 3D Printed Prototype, and Evaluation. J Healthc Eng. May 10, 2018;2018:8937985. doi:10.1155/2018/8937985. PMID: 29861884; PMCID: PMC5971329.

(Continued)

*Primary Examiner* — Joseph D. Boecker
(74) *Attorney, Agent, or Firm* — The Roy Gross Law Firm, LLC; Roy Gross

(57) ABSTRACT

An neonatal care unit comprising: a hood defining an interior space and having a bottom opening, wherein the hood is dimensioned to accommodate a neonate; a sealing skirt extending along at least a portion of a peripheral edge of the bottom opening and configured to engage at least part of a front torso region of a human in a sealing engagement; at least one access opening located about a sidewall of the hood and dimensioned to allow passage of the neonate therethrough; at least two arm ports located about the sidewall and dimensioned to allow passage of a hand therethrough; and at least one port configured to allow passage of a medical conduit therethrough.

19 Claims, 5 Drawing Sheets

(52) U.S. Cl.
CPC . *A61M 16/0627* (2014.02); *A61M 2202/0208* (2013.01); *A61M 2240/00* (2013.01)

(58) Field of Classification Search
CPC .. A61M 2240/00; A61M 16/00; A61M 16/06; A61M 16/0627; A61M 16/10; A61M 16/16; A61B 2503/045; A62B 17/04; A62B 17/08
See application file for complete search history.

(56) References Cited

U.S. PATENT DOCUMENTS

| | | | |
|---|---|---|---|
| 2006/0206978 A1* | 9/2006 | Hilton | A41D 1/215 2/104 |
| 2009/0012349 A1* | 1/2009 | Willemsen | A61G 11/00 600/22 |
| 2013/0025062 A1* | 1/2013 | Esch | A61G 7/065 5/655 |
| 2013/0204074 A1* | 8/2013 | Belval | A61G 1/042 600/22 |
| 2016/0074268 A1* | 3/2016 | Breegi | A61G 11/009 600/21 |
| 2019/0254901 A1 | 8/2019 | Fernandes et al. | |
| 2021/0386501 A1* | 12/2021 | Rondoni | A61M 16/0627 |

OTHER PUBLICATIONS

Karlsson V, Heinemann AB, Sjörs G, Nykvist KH, Agren J. Early skin-to-skin care inextremely preterm infants: thermal balance and care environment. J Pediatr. 2012;161(3):422-426. doi:10.1016/j.jpeds.2012.02.034.

Johnston C, Campbell-Yeo M, Disher T, Benoit B, Fernandes A, Streiner D, Inglis D, Zee R. Skin-to-skin care for procedural pain in neonates. Cochrane Database Syst Rev. Feb. 16, 2017;2(2):CD008435. doi: 10.1002/14651858. CD008435.pub3. PMID: 28205208; PMCID: PMC6464258.

WHO Immediate KMC Study Group. Impact of continuous Kangaroo Mother Care initiated immediately after birth (iKMC) on survival of newborns with birth weight between 1.0 to < 1.8 kg: study protocol for a randomized controlled trial. Trials. Mar. 19, 2020;21(1):280. doi: 10.1186/s13063-020-4101-1. PMID: 32188485; PMCID: PMC7081677.

Sehgal A, Nitzan I, Jayawickreme N, Menahem S. Impact of Skin-to-Skin Parent-Infant Care on Preterm Circulatory Physiology. J Pediatr. Jul. 2020;222:91-97.e2. doi: 10.1016/j.jpeds.2020.03.041. Epub May 7, 2020. PMID: 32389414.

Novonate. (2019). Stanford Byers Center for Biodesign. [https://biodesign.stanford.edu/our-impact/technologies/novonate.html].

PCT International Search Report for International Application No. PCT/IL2021/051211, mailed Jan. 25, 2022, 3pp.

PCT Written Opinion for International Application No. PCT/IL2021/051211, mailed Jan. 25, 2022, 5pp.

PCT International Preliminary Report on Patentability for International Application No. PCT/IL2021/051211, issued Mar. 28, 2023, 6pp.

* cited by examiner

PREMATURE INFANT CARE SYSTEM

CROSS-REFERENCE TO RELATED APPLICATIONS

This application is a National Phase of PCT Patent Application No. PCT/IL2021/051211 having International filing date of Oct. 10, 2021, which claims the benefit of priority of British Patent Application No. 2016124.6, filed Oct. 11, 2020, entitled: "PREMATURE INFANT CARE SYSTEM", all of which are hereby incorporated by reference in their entirety.

FIELD OF THE INVENTION

Some embodiments of the present invention relate in general to the field of neonatal care. More specifically, embodiments of the presented invention are related to a neonatal care unit to be used during a skin-to-skin holding.

BACKGROUND

Preterm infants often require hospitalization and some require the care of a neonatal intensive care unit (NICU). Skin-to-skin holding has been reported as a valuable intervention for preterm infants. Current understanding of the effects of the parent body on preterm infant development suggests that the physical cradle of the parent's chest and arms during skin-to-skin holding has a profound effect on the development of the newborn's brain as well as on the parenting process. Recent studies report the long-term effects of skin-to-skin holding include a greater head circumference and significant improvement in motor and cognitive development at one year of age.

However, skin-to-skin holding of premature infants poses challenges with respect to the actual transfer of the baby, maintaining and controlling environmental parameters such as temperature, humidity, and providing continuously life support and monitoring connections.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, an neonatal care unit comprising: a hood defining an interior space and having a bottom opening, wherein the hood is dimensioned to accommodate a neonate; a sealing skirt extending along at least a portion of a peripheral edge of the bottom opening and configured to engage at least part of a front torso region of a human in a sealing engagement; at least one access opening located about a sidewall of the hood and dimensioned to allow passage of the neonate therethrough; at least two arm ports located about the sidewall and dimensioned to allow passage of a hand therethrough; and at least one port configured to allow passage of a medical conduit therethrough.

There is also provided, in an embodiment, a method comprising: providing an neonatal care unit comprising: a hood defining an interior space and having a bottom opening, wherein the hood is dimensioned to accommodate a neonate, a sealing skirt extending along at least a portion of a peripheral edge of the bottom opening and configured to engage at least part of a front torso region of a human in a sealing engagement, at least one access opening located about a sidewall of the hood and dimensioned to allow passage of the neonate therethrough, at least two arm ports located about the sidewall and dimensioned to allow passage of a hand therethrough, and at least one port configured to allow passage of a medical conduit therethrough; positioning the neonatal care unit about a front torso region of a human, such that the sealing skirt engages at least part of the front torso region in a sealing engagement; placing a neonate within the interior space, wherein the neonate is passed into the interior space through the access opening; and passing at least one medical conduit through the at least one port.

In some embodiments, the hood is made of a transparent polymer.

In some embodiments, the hood is dimensioned to fit within the front torso region, such that all of the sealing skirt engages the front torso region.

In some embodiments, the hood comprises a double-layer construction.

In some embodiments, the sealing skirt extends at least 85% of a length of the peripheral edge.

In some embodiments, the sealing skirt is made of an elastic material.

In some embodiments, the sealing skirt is an inflatable sealing skirt.

In some embodiments, the access opening comprises a door which may be opened and closed, and wherein a periphery of the door comprises a sealing element which engages a periphery of the access opening in a sealing engagement. In some embodiments, the placing comprises (i) opening the door, (ii) passing the neonate through the access opening into the interior space, and (iii) closing the door.

In some embodiments, the door is located about the sidewall at a distal end of the hood.

In some embodiments, the door comprises a double-layered construction.

In some embodiments, the at least two arm ports are located on opposite sides of the hood.

In some embodiments, each of the at least two arm ports comprises a sealing membrane configured to at least partially sealingly engage a periphery of an arm entering through the arm port.

In some embodiments, the medical conduit is one of: a tube, a cable, a connector, a wire, a liquid carrier, a gas carrier, an electrical wire, a monitoring cable, a viewing cable, and a data cable.

In some embodiments, the medical conduit is associated with at least one medical monitoring device configured to measure one of: ambient air temperature, body temperature, air humidity, neonate respiration, neonate cardiac function, neonate blood oxygenation, neonate brain activity, neonate blood pressure, neonate cardio-respiratory activity.

In some embodiments, the medical conduit is associated with at least one of: an intravenous pump, an oxygen supplementation system, a continuous positive airway pressure system, a feeding tube, an umbilical artery catheter, a fluid transport device, a hemofiltration system, and a hemodialysis system.

In some embodiments, the medical conduit is associated with at least one of: ventilation, air conditioning, air humidification, and air heating.

In some embodiments, the neonatal care unit further comprises a heating element and a control unit configured to operate the heating element to heat the interior space to a specified temperature.

In some embodiments, the neonatal care unit further comprises one or more straps configured to extend around the torso and operably connect using securing means. In some embodiments, the method further comprises extending the one or more straps around the torso and operably connecting the straps using the securing means.

In some embodiments, the neonatal care unit further comprises an infrared reflective coating applied to an interior surface of the hood, other than the access opening, the at least two arm ports, and the at least one port.

In some embodiments, the neonatal care unit further comprises an infrared reflective cover configured to be positioned over the hood and cover an exterior surface of the hood, other than the access opening, the at least two arm ports, and the at least one port. In some embodiments, the method further comprises positioning the cover over the hood.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
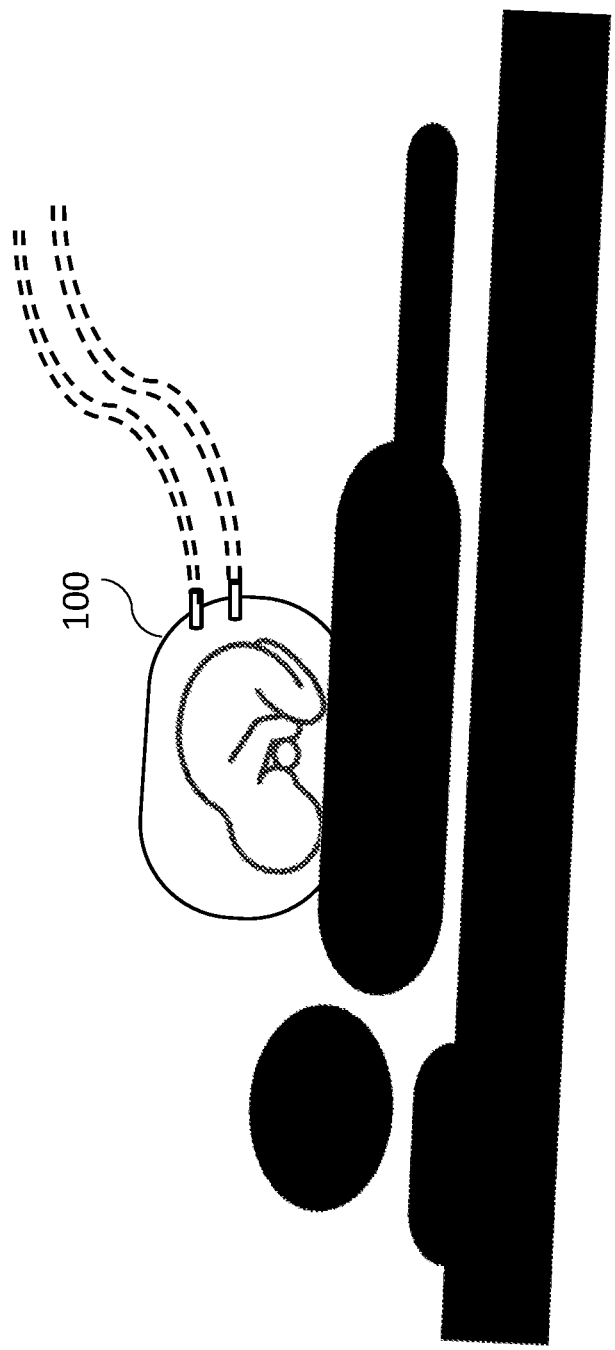
FIG. 1 illustrates a neonatal care unit of the present disclosure, in accordance with some embodiments of the present invention.

Disclosed are a neonatal care unit and associated method providing a neonatal care unit for premature infants, preterm infants, and/or low birth weight term infants.

In some embodiments, the present care unit provides for a compact neonatal care capsule which may be placed in close proximity to a body of a caregiver (e.g., a parent), to provide for prolonged skin-to-skin care within a controlled environment, in the NICU or outside of a traditional NICU. In some embodiments, the present care unit is a portable open-bottomed unit configured for placing about a bare torso or chest of a caregiver in a substantially sealed engagement, so as to provide for controlled environment for skin-to-skin care to the neonatal accommodated therein. In some embodiments, the care unit provides for a regulated environment particularly suitable for the continuous care of preterm infants.

As noted above, skin-to-skin holding has been reported as a valuable intervention for preterm infants. Current understanding of the effects of the parent body on preterm infant development suggests that the physical cradle of the parent's chest and arms during skin-to-skin holding has a profound effect on the development of the newborn's brain as well as on the parenting process. Recent studies report the long-term effects of skin-to-skin holding include a greater head circumference and significant improvement in motor and cognitive development at one year of age.

The benefits of skin-to-skin holding are widely regarded as a valuable intervention for preterm infants. However, simply holding preterm infants outside of a regulated environment care unit may present particular challenges and risks for the preterm infants, which have several significant disadvantages compared to term infants, specifically with respect to heat retention and hydration regulation.

Preterm infants have little insulating subcutaneous fat compared to term infants, making them far more susceptible to heat loss. In addition, preterm infants have very thin skin leading to significant trans-epidermal water loss and evaporative heat loss. The thin keratinized layer can be completely absent in infants until the 26th week, making their skin permeable to water. Moreover, preterm infants can have excessive amounts of evaporative heat loss due to a greater surface area to volume ratio. Because of the lack of significant insulating subcutaneous fat, heat can be more easily lost from internal organs to skin, leading to more rapid decrease in internal temperature. In infants born very prematurely, such as at 25-27 weeks, evaporative heat loss can be, in some cases, the most important mode of heat loss for more than 10 days after birth. In addition, preterm infants can have blood vessels close to skin, leading to an increased rate of heat loss.

In addition to their increased risk for heat loss, preterm infants can also have very poor mechanisms for body temperature regulation, and can be far more limited than term infants in generating heat. Preterm infants can lack the shivering mechanism used to maintain body temperature. In addition, a term infant's reaction to rapid temperature fluctuations upon birth can include increased voluntary muscular activity which can be mostly absent in very preterm infants. Brown fat used for non-shivering thermogenesis can be significantly more limited in preterm infants, and thus more calories intended for natural growth are diverted to heat generation.

Thus, protecting infants from heat loss and providing appropriate thermoregulation can be one of the most important goals in the NICU. Improved thermoregulation can increase preterm infant chances of survival, reduce infant need to perform heat producing metabolic work using energy intended for growth and development, and eliminate problems and complications associated with rewarming of cold infants.

In the womb, a significant pathway for absorption of amniotic fluid by the fetus is through diffusion of fluid across the fetal skin back into fetal circulation. This pathway of absorption of water is generally referred to as the Intramembranous Pathway. Fluid constantly absorbed by the fetus can be mostly urinated and circulated back into the amniotic sac. Upon preterm birth, the underdeveloped skin can be exposed to a harsh and dry environment of a nursery, where the intramembranous pathway of absorption of fluid is halted and even reversed through tremendous evaporative loss. Specifically, the skin of infants born 23 to 26 weeks' gestation is generally extremely immature and can be ineffective as an epidermal water barrier. This can lead to disturbances in temperature regulation, water balance and breakdowns in skin integrity. Thus, premature infants who are less than about 30 weeks gestational age can exhibit water loss of as much as 15 times greater than that of full-term infants because of their immature stratum corneum.

A potential advantage of the present disclosure is, therefore, in that it provides for a regulated, protective, and insulated portable capsule in which a neonate may be accommodated in close proximity to the bare body of a caregiver, and thus provided with skin-to-skin care for prolonged periods, with no risk to the neonate. The present care unit present simple and cost-effective construction, and may offer a practical solution for use in developed as well as developing countries.

FIG. 1 illustrates a neonatal care unit 100 of the present disclosure. Unit 100 is shown as an open-bottomed capsule or hood placed about an upper body area (e.g., chest) of a caregiver, generally in a lying down or reclined position, e.g., on a bed. Unit 100 may provide for a regulated environment suitable for the care of preterm neonates, including, without limitation, thermal regulation, humidity regulation, air circulation regulation, respiratory support, other and/or additional life supporting and/or monitoring equipment and connections.

In some embodiments, unit 100 is open-bottomed, such that a neonate accommodated therein may experience skin-to-skin contact with the caregiver on whose body unit 100 is placed, while the care unit creates a protective capsule surrounding the neonate and engaging the body of the caregiver in a peripheral sealing engagement. In some embodiments, a bottom periphery of unit 100 comprises at least partial sealing elements, e.g., a sealing skirt (shown in FIGS. 2, 3 and 4), to at least partially seal a bottom periphery of unit 100 against the body region of the caregiver, so as to protect an interior of care unit 100 against the ambient environment and allow for maintaining necessary or desired environmental parameters inside unit 100 within a desired range of values, as may be necessary to support the life and well-being of the neonate.

Figure 2:
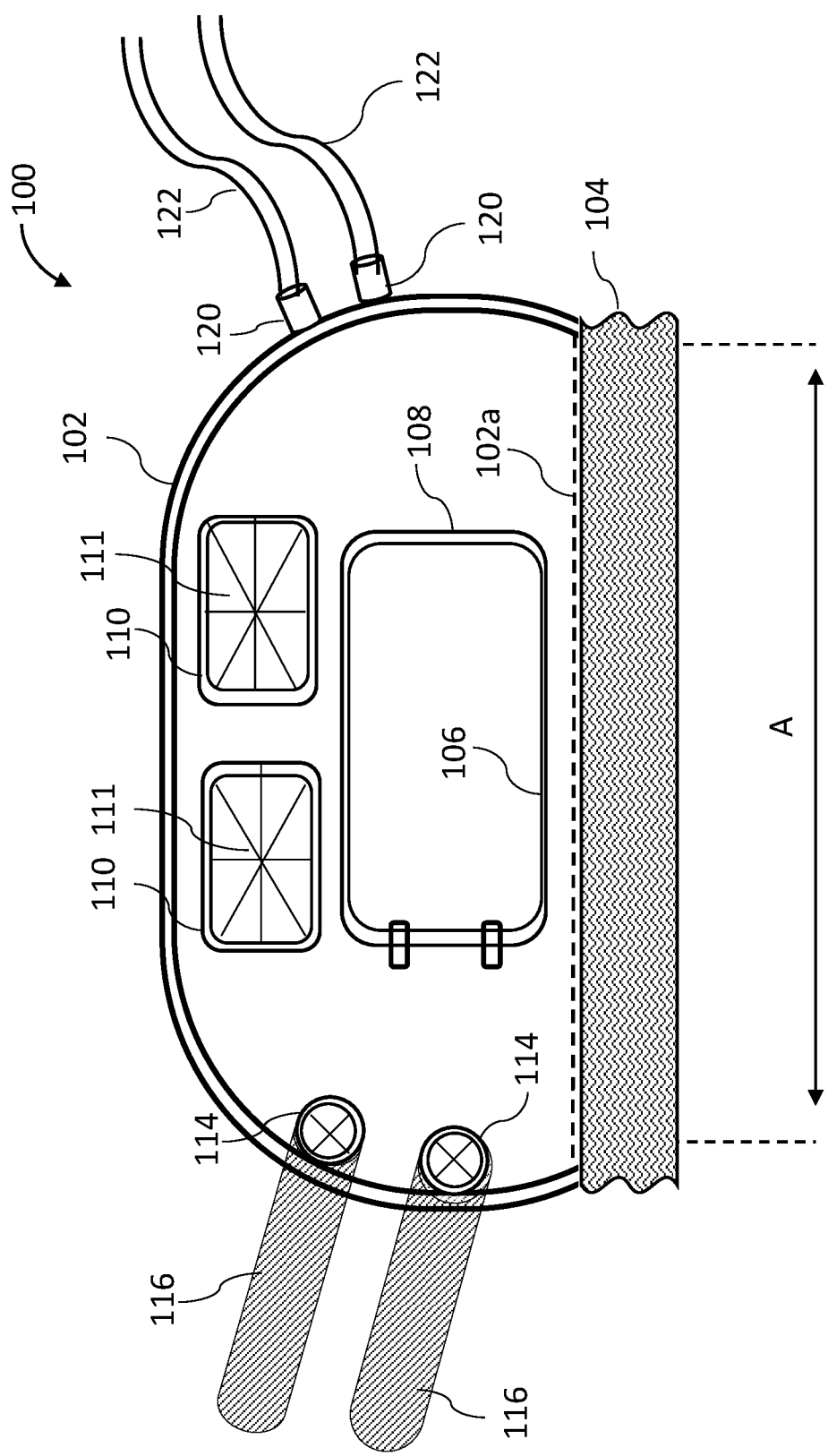
FIG. 2 is a side view of an exemplary neonatal care unit, in accordance with some embodiments of the present invention.
Figure 3:
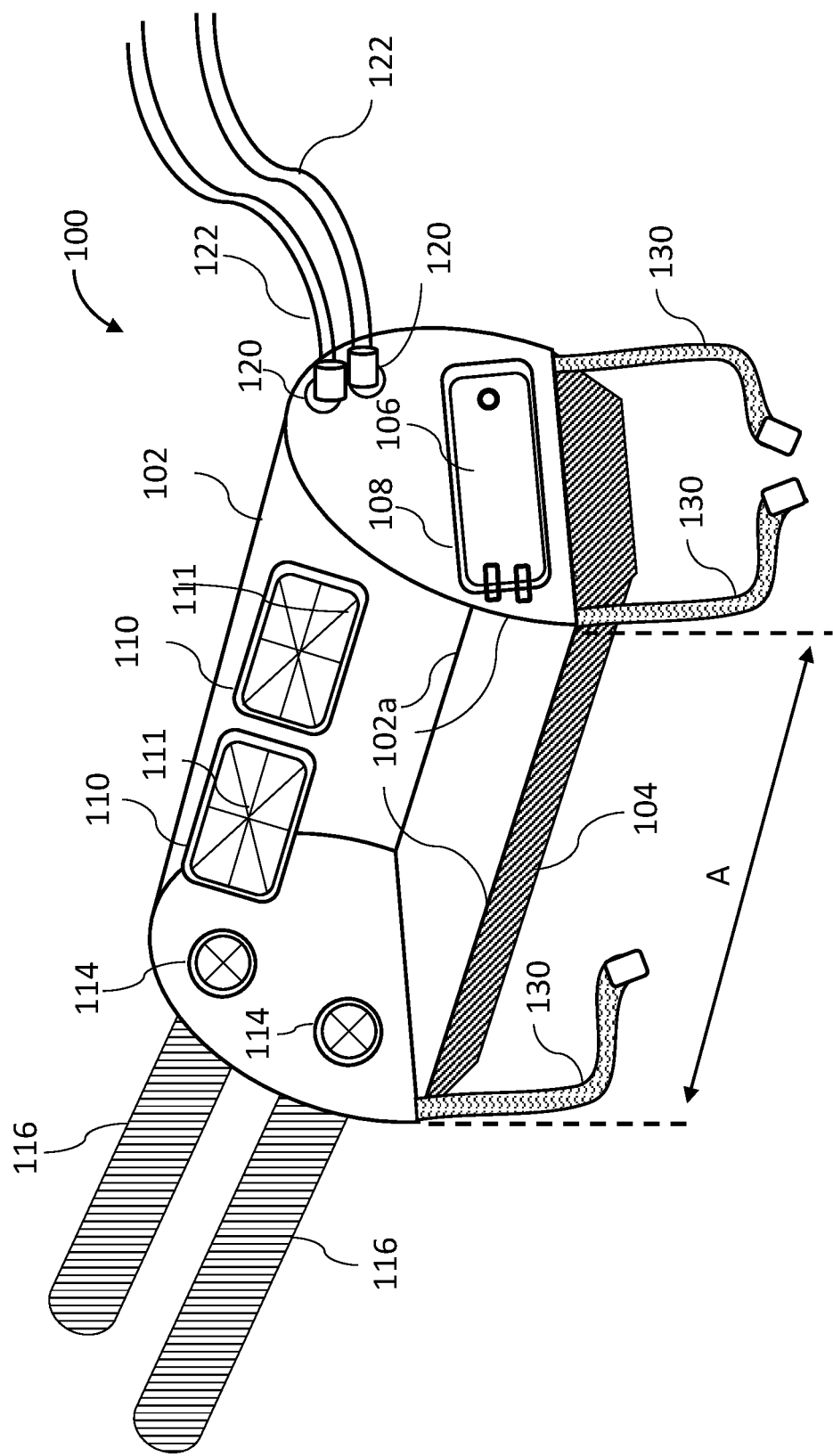
FIG. 3 is a perspective view of another exemplary neonatal care unit, in accordance with some embodiments of the present invention.

FIG. 2 is a side view, and FIG. 3 is a perspective view, of neonatal care units 100, according to some embodiments of the present disclosure.

In some embodiments, neonatal care unit 100 comprises a hood 102, which may resemble a cover or a capsule defining a sidewall, an upper end, and a bottom-side opening A. Hood 102 may be designed and dimensioned to accommodate a neonate therein. In some embodiments, hood 102 is a compact hood dimensioned to fit closely around a neonate and accommodate it therein within a minimal interior volume, such that, e.g., an umbilical cord stump of the neonate may be extended past an opening in hood 102. Thus, the stump may be accessed externally of hood 102 in order to insert a catheter, such as a peripherally inserted central catheter (PICC line), and/or any other suitable medical tubing. In this way, venous access may be established, and the neonate may be supplied with IV, medication, fluids, and/or nutrition, without the need to access the interior of hood 102 and potentially disturb the regulated environment therein.

In some embodiments, hood 102 has a bottom peripheral edge 102a dimensioned to fit and engage an area of the upper body (e.g., chest) of a caregiver. In some embodiments, bottom peripheral edge 102a of hood 102 defines a generally flat plane. In some embodiments, bottom peripheral edge 102a may be profiled to follow generally the contours of a human chest area. In some embodiments, a plurality of peripheral edge contours of hood 102 may be used, to, e.g., conform to female or male users.

In some embodiments, hood 102 may be an oval or oblong hood, box like, dome-like, curvilinear, prismatic, or any similar shape. Hood 102 may be dimensioned to accommodate neonates of varying sizes, as well as one or more equipment units, as may be detailed below. In some embodiments, hood 102 has a length of between 25-45 cm, width of between 15-30 cm, and height of between 15-20 cm.

Hood 102 may comprise materials and construction configured to isolate a neonate from the ambient environment, and to maintain regulated internal temperature, humidity, oxygen concentration, and the like. In some embodiments, hood 102 allows retaining and maintaining regulated environment within care unit 100, and physically protects the neonate from the external environment.

In some embodiments, hood 102 is constructed of an impermeable transparent material, to enable observation of the neonate from at least two directions, by the treating nurse and the holding parent. In some embodiments, hood 102 may be rigid, semi-rigid, or flexible. In some embodiments, portions of hood 102 may be rigid, semi-rigid, and/or flexible. In some embodiments, any suitable synthetic resin or polymer may be used in the construction of hood 102. In some embodiments, hood 102 may be made of a thermoplastic or thermosetting polymer using an injection molding process. In some embodiments, hood 102 comprises a double-layer construction to promote insulation, wherein two layers of material may be interspersed with a thin layer of, e.g., a specified gas. In some embodiments, hood 102 comprises a composite material. For example, hood 102 may be made from a medical grade polymer according to ISO 10993, for example, medical grade polycarbonate.

In some embodiments, hood 102 comprises a sealing skirt 104 attached along at least a portion of a length of bottom peripheral edge 102a thereof. In some embodiments, skirt 104 may be configured to seal, at least in part, any gap formed between the peripheral bottom edge of hood 102 and the body contours of the caregiver. In some embodiments, sealing skirt 104 is configured to provide sufficient sealing between the hood and the caregiver's body, as to allow to maintain and control the environment inside the hood. For example, sealing skirt 104 may provide sufficient sealing for maintaining and controlling the temperature, humidity and/or airflow inside the hood. The temperature, humidity and/or airflow may be monitored and controlled based on monitored parameters, as discussed herein below.

In some embodiments, skirt 104 may comprise a peripheral skirt which depends generally downwardly and/or radially from peripheral bottom edge 102a. Skirt 104 may comprise an integral continuous skirt circumscribing the bottom peripheral edge 102a in its entirety. However, in some embodiments, skirt 104 may comprise two or more, or a plurality, of individual skirt sections or strips, each extending a portion of the bottom peripheral edge 102a. In some embodiments, skirt 104 is made of any suitable flexible sealing material, e.g., a thermoplastic elastomer, silicone rubber, and the like, which may conform to the contours of the caregiver's body when unit 100 is placed about an upper body region of the caregiver, as may be seen in FIG. 1. In some embodiments, skirt 104 and/or portions thereof may be over-molded onto the bottom edge 102a. In other embodiments, skirt 104 may be attached to bottom edge 102a, e.g., inserted into a corresponding slot defined in bottom edge 102a. In other embodiments, skirt 104 may be welded to bottom edge 102a, e.g., by ultrasonic welding. In other embodiments, skirt 104 may be glued to bottom edge 102a, e.g., using any suitable adhesive. In some embodiments, skirt 104 may extend, continuously or intermittently, at least 85% of a length of bottom edge 102a. in some embodiments, sealing skirt 104 may an inflatable sealing skirt. In such case sealing skirt 104 may include one or more inflating/deflating opening for insertion/extraction of an inflating medium (e.g., gas, liquids, etc.). In nonlimiting example, sealing skirt 104 may include a medical grade polycarbonate. In another nonlimiting example, sealing skirt 104 may include a medical grade silicone sheet.

In some embodiments, skirt 104 is included in a garment to be worn by the caregiver (e.g., parent) holding the neonate. Such a garment may include strips/sleeves connected to skirt 104 and configured to attach the skirt to the caregiver's body. In some embodiments, the garment comprising skirt 104 includes a hole substantially in the size of bottom opening A, allowing bottom peripheral edge 102a of hood 102 to be covered by skirt 104 while the caregiver's torso is uncovered and the baby can be in skin-to-skin contact. In some embodiments, hood 102 may include one of more connectors for connecting the hood (e.g., peripheral edge 102a) to skirt 104 included in the garment. The connectors may include any suitable means for connecting a skirt to a hood. In some embodiments, the garment may be made from an elastic material (e.g., a silicone-based elastomer or any other elastomer or an elastic fabric) and the hole in garment may have substantially smaller (e.g., smaller in 10%) circumference than the circumference of bottom opening A. Therefore, when peripheral edge 102a of hood 102 is inserted into the hole in skirt 104, the skirt may slightly starch, providing sufficient sealing between the caregiver's body and the hood.

In some embodiments, hood 102 may comprise at least one access door 106 located within an opening 108 in a sidewall of hood 102. In some embodiments, door 106 may be located about a side region of a sidewall of hood 102. In other embodiments, as can be seen in FIG. 3, door 106 may be located about a distal end region of hood 102, wherein the distal end defines a region of hood 102 farthest for the head of a caregiver when care unit 100 is in use as shown in FIG. 1.

In some embodiments, door 106 may be opened and closed to provide access to the interior of hood 102, e.g., to bring in a neonate to be accommodated within hood 102. In some embodiments, door 106 comprises double-layer construction. In some embodiments, a periphery of door 106 comprises a sealing element (e.g., hook-and-loop fastener) to ensure hermetic sealing of opening 108 when door 106 is closed. In nonlimiting example, door 106 is made from polyvinyl chloride coated from the inside by a transparent medical sticker.

In some embodiments, hood 102 comprises one or more arm ports 110 at its sidewall, for accessing and manipulating the neonate from a variety of positions, while maintaining the protection of hood 102 over the neonate. In some embodiments, a pair of arm ports 110 may be located, e.g., at a first side of a sidewall of hood 102, as shown in FIGS. 2 and 3, or each port in the pair may be located on opposite sides thereof. In some embodiments, arm ports 110 may allow the arms of a caregiver and/or medical practitioner to enter care unit 100, for purposes of providing various treatments, medical care, and/or medical examination to the neonate.

In some embodiments, hood 102 comprises one or more strips or straps for securing the neonate to the caregiver's body. The one or more strips may include adjustable fasteners allowing to adjust the length of the straps and to fasten the neonate to the caregiver's body.

In some embodiments, arm ports 110 may be provided with a sealing membrane 111 configured to at least partially sealingly engage a periphery of arms entering through arm ports 110. In some embodiments, sealing membrane 111 may be elastic membrane provides with a plurality of slits to allow passage of hand and forearm therethrough, and sealingly engage an exterior periphery thereof. In some embodiments, when hood 102 comprises a double-layered construction, each arm port 110 may comprise two sealing membranes 111, each corresponding to one layer of hood 102.

In some embodiments, hood 102 may be provided with one or more ports 114 configured to permit passage of conduits or leads, e.g., conduits 116 for infusion or monitoring. For example, one conduit 116 may provide air enriched with oxygen to hood 102. In some embodiments, ports 114 may be provided with sealing joints as known in the art. In some embodiments, at least one of ports 114 may be located in close proximity to access door 106.

In some embodiments, hood 102 may include a conduit 116 having a short tube comprising a mouthpiece enabling the caregiver to exhale humidified air into hood 102. The air provided by the caregiver is naturally reach with humidity.

In some embodiments, hood 102 may be provided with one or more connections 120 for connecting and or permitting passage of one or more medical measurement and observation systems (including sensors and/or monitors) of, e.g., temperature, respiration, cardiac function, oxygenation, brain activity such as ECG (electrocardiography) monitor, blood pressure monitor, cardio-respiratory monitor, pulse oximeter, etc. In some embodiments, connections 120 include communication ports, electrical ports, fluid connectors and the like.

In some embodiments, care unit 100, e.g., hood 102, may be provided with one or more openings, ports, and/or connections 120 for engaging life supporting equipment with care unit 100, e.g., with tubing 122. Tubing 122 may be selected from, medical tubing, electrical wires, communication wires (e.g., optical fibers) and may be configured to connect care unit 100 with any required devices, conduits, liquid sources, needles, sensors, monitors, etc., that are used by medical personal in association with the neonate. Such equipment may include all tubes, cables, connectors, wires, liquid carriers, gas carriers, electrical wires, monitoring cables, viewing cables, data cables, etc., that may be used in connection to life support equipment, medical equipment or physical environment maintenance or monitoring in connection with care unit 100.

In some embodiments, medical equipment and systems used in connection with care unit 100 may include, e.g.:
  IV (intravenous) pump, oxygen supplementation systems; by head hood or nasal cannula; continuous positive airway pressure system; a feeding tube; an umbilical artery catheter; a fluid transport device; hemofiltration system; hemodialysis system;
  Medical measurement and observation systems (including sensors and/or monitors) of temperature, respiration, cardiac function, oxygenation, brain activity such as ECG (electrocardiography) monitor, blood pressure monitor, cardio-respiratory monitor, pulse oximeter; and
  Environmental control systems such as ventilator, air conditioner, humidifier, temperature regulator, climate control systems, noise muffling device, vibration muffling device, etc.

For example, in some embodiments, care unit 100, e.g., hood 102, may be provided continuously with air circulation and distribution, e.g., through a conduit 116 connected to hood 102 through a port 114. In some embodiments, air circulation may be provided by a ventilation unit, e.g., a fan, a blower, a compressor, a pump, air streamer, propeller, ventilator, and the like, connected to ventilate the neonate with a continuous flow of filtered, oxygenated, tempered and humidified air. In some embodiments, care unit 100 may be provided with a gas line circuit for administering a medicinal gaseous mixture to the neonate inside hood 102. In some embodiments, an oxygen line may be connected to care unit 100, e.g., through a port 114 or connection 120.

In some embodiments, care unit 100 may be provided with one or more sensors configured to measure one or more parameters associated with care unit 100, e.g., at least one of air temperature, neonate temperature, air humidity, air composition, oxygen levels, $CO_2$ concentration, pressure, light, motion, sound. In some embodiments, care unit 100 may be configured to provide indications with respect to the measured parameters, e.g., when one or more measured parameter deviates from a predetermined value or range of values. In some embodiments, such indications may be visual or audible, e.g., sounding an alarm or alert of flashing a warning light. In some embodiments, such indications (e.g., from ambient sensor and/or baby related sensors) may change automatically air flow, air humidity and temperature, or open or close ventilation ports in order to restore the variable to the desired range in a closed loop manner.

In some embodiments, care unit 100 may comprise a thermal unit (not shown) configured to generate and maintain the temperature within hood 102 at a predetermined level or range of levels. In some embodiments, the thermal unit may be an electric heater having a control configured to vary the heat output of the heater to heat the internal air and/or walls of hood 102 to the selected temperature. In other embodiments, the thermal unit may consist of an infrared heater, a water/oil-heated radiator, a coiled heater, a quartz tube air heater, a capacitor-type heater, and the like. In some embodiments, hot and humidified air circulation may be provided by conduits 116 via ports 114. In some embodiments, hot and humidified air circulation may be provided by the hot and humidified air used for noninvasive respiratory support of the infant. In some embodiments humidification can be provided by a tube with a mouthpiece enabling the caregiver to exhale humidified air into the hood.

Figure 4:
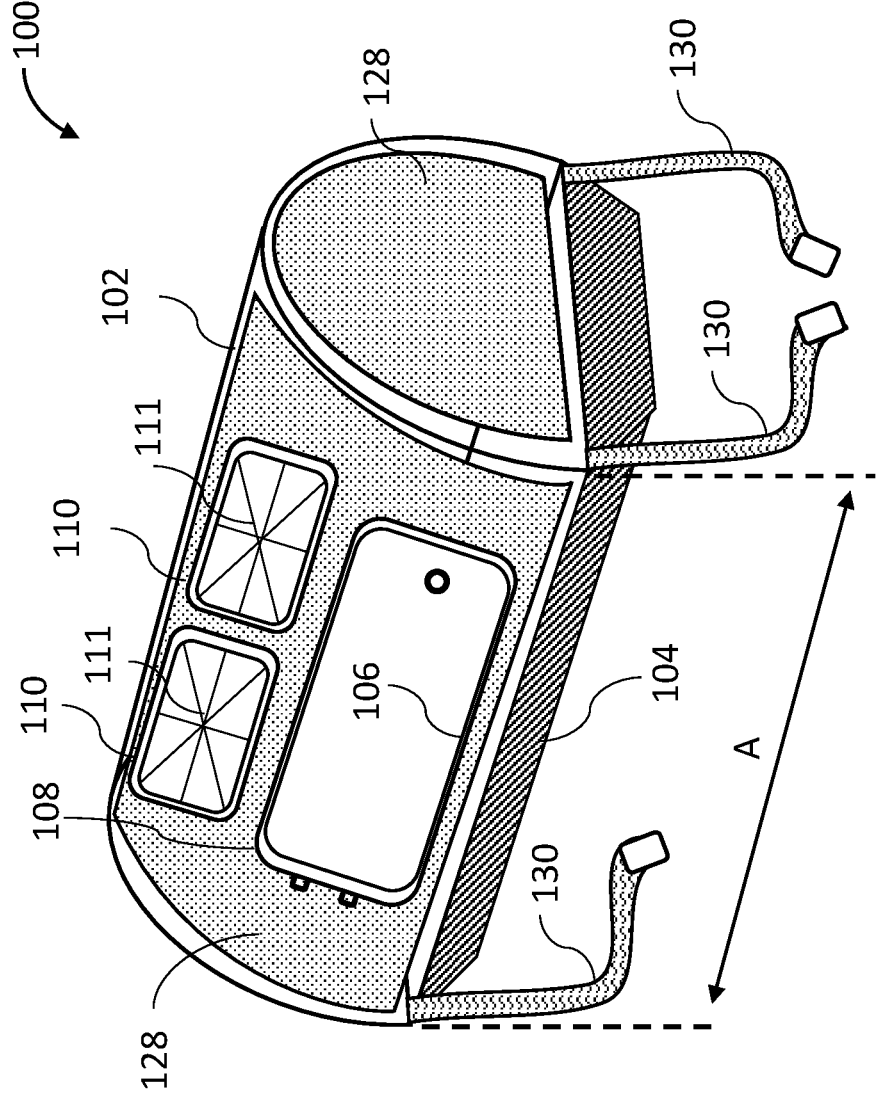
FIG. 4 is another perspective view of a neonatal care unit, in accordance with some embodiments of the present invention.

FIG. 4 illustrates an embodiment of the present disclosure wherein an interior of hood 102 may be provided, at least in part, with infrared reflective coating 128, configured to reflect IR radiation, e.g., body heat from the caregiver and/or the neonate, back towards the interior of hood 102, and thus to reduce the heat transfer from the interior of hood 102 into the ambient environment and mitigate any heat loss from the neonate accommodate therein. In some embodiments, IR reflective coating 128 covers internal areas of hood 102 other than, e.g., openings and ports such as opening 108, arm ports 110, ports 114, and/or connections 120. In some embodiments, care unit 100 may include one or more reflective coatings 128 placed at one or more of the walls of hood 102, as illustrated. In some embodiments, reflective coatings 128 may cover at least 80% of the surface of hood 102, or may cover only one or two walls of hood 102. In some embodiments, reflective coatings 128 may include polymeric sheets coated with IR reflective pigments. Alternatively, the IR reflective pigments may be directly coated on the walls/cover of hood 102. In some embodiments, IR reflective coatings 128 may be transparent in the visible spectrum. For example, IR reflective coatings 128 may include a multilayered film comprising three thin layers of dielectric/metal/dielectric materials. In yet another example, IR reflective coatings 128 may include two polymeric layers which differ in refractive index by at least about 0.03, the polymeric layers having an optical thickness of between about 0.09 µm and 0.45 µm.

Alternatively, in some embodiments, there is provided an IR reflective cover (not illustrated) configured to be positioned over hood 102 and to reflect IR radiation emanating from hood 102. In some embodiments, the reflective cover extends over the exterior of hood 102, other than, e.g., openings and ports such as opening 108, arm ports 110, ports 114, and/or connections 120. In some embodiments, the IR reflective cover may include substantially the same materials as IR reflective coatings 128, as discussed herein above.

In some embodiments, the reflective coating and/or reflective cover may be configured to concentrate the reflected IR radiation about an approximated location of a neonate within hood 102 when it is in use.

With reference back to FIG. 3 and FIG. 4, in some embodiments, care unit 100 comprises one or more means for securing care unit 100 to a caregiver, so as to prevent movement and dislocation of care unit 100 when is use and placed about a body region of a caregiver. For example, in some embodiments, care unit 100 may comprise one or more straps 130 configured to extend around the torso of a caregiver and operably connect using securing means.

Figure 5:
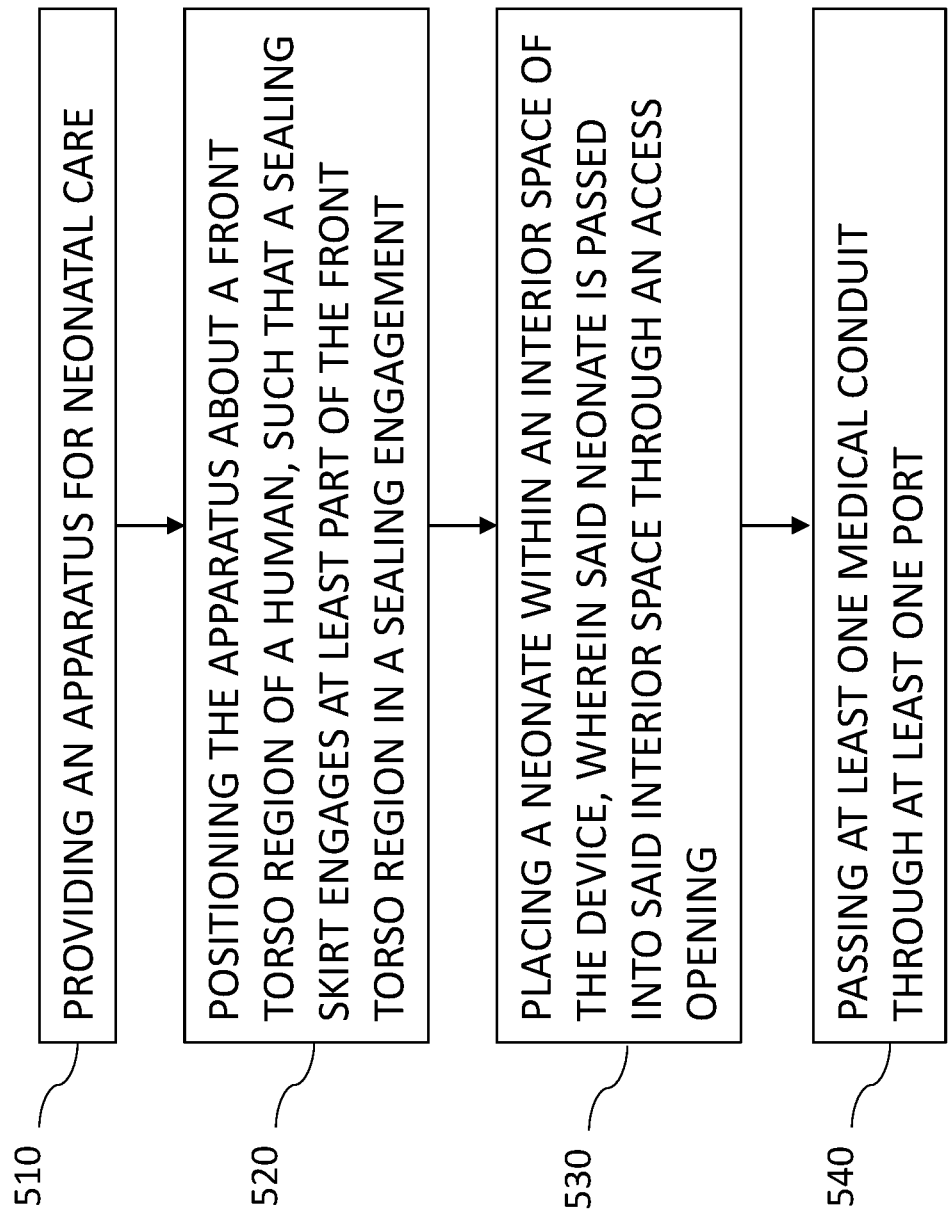
FIG. 5 is a flowchart of a method of neonatal caring according to some embodiments of the invention.

Reference is now made to FIG. 5 which is a flowchart of a method for neonatal caring according to some embodiments of the invention. In step 510, a neonatal care unit for neonatal care may be provided, for example, neonatal care unit 100 disclosed herein above. In step 520, neonatal care unit 100 may be positioned about a front torso region of a human, such that a sealing skirt (e.g., sealing skirt 104) engages at least part of the front torso region in a sealing engagement. In step 530, a neonate is placed within an interior space of neonatal care unit 100. The neonate is passed into the interior space of device through an access opening, for example, door 106. In step 540, at least one medical conduit (e.g., conduits 116 and/or 122) may be passed through at least one port included in neonatal care unit 100.

In some embodiments, the method may further include monitoring at least one parameter of the neonate using at least one sensor included in the neonatal care unit. For example, sensors included in neonatal care unit 100 may monitor at least one of, ambient air temperature, body temperature, air humidity, neonate respiration, neonate cardiac function, neonate blood oxygenation, neonate brain activity, neonate blood pressure, neonate cardio-respiratory activity. In some embodiments, the monitored at least one parameter may use to control, by a controller associate with neonatal care unit 100, the provision of at least one of: a medication, heat, humidity, nutrition and ventilation ports. The controller may receive a signal form at least one of the sensors (e.g., hood ambient sensors and/or neonate monitoring sensors) and may change, automatically at least one of the working parameters of, a heating unit, ventilation ports, a pump supplying air, pump/valve supplying nutrition/blood, amount of humidity and the like. For example, hot and humid air may be provided in measured temperature and humidity are less than the required threshold. In another example, air enriched with oxygen/or direct provision of oxygen may be provided if the saturation level of the neonate is lower than 90.

In some embodiments, the monitored parameters may allow caregiver and/or medical practitioner to monitor the life signs of the neonate during the skin-to-skin holding under neonatal care unit 100.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A neonatal care unit comprising:
   a hood defining an interior space and having a bottom opening, wherein said hood is dimensioned to accommodate a neonate;
   a sealing skirt extending along at least a portion of a peripheral edge of said bottom opening and configured to engage at least part of a front torso region of a human in a sealing engagement;
   at least one access opening located about a sidewall of said hood and dimensioned to allow passage of said neonate therethrough;
   at least two arm ports located about said sidewall, wherein each arm port is dimensioned to allow passage of a hand therethrough; and
   at least one port configured to allow passage of a medical conduit therethrough.

2. The neonatal care unit according to claim 1, wherein said hood comprises a double-layer construction.

3. The neonatal care unit according to claim 1, wherein said sealing skirt extends at least 85% of a length of said peripheral edge.

4. The neonatal care unit according to claim 1, wherein said sealing skirt is made of an elastic material.

5. The neonatal care unit according to claim 1, wherein said sealing skirt is an inflatable sealing skirt.

6. The neonatal care unit according to claim 1, wherein said at least one access opening comprises a door which may be opened and closed, and wherein a periphery of said door comprises a sealing element which engages a periphery of said at least one access opening in a sealing engagement.

7. The neonatal care unit according to claim 1, wherein each of said at least two arm ports comprises a sealing membrane configured to at least partially sealingly engage a periphery of an arm entering through said arm port.

8. The neonatal care unit according to claim 1, wherein said medical conduit is one of: a tube, a cable, a connector, a wire, a liquid carrier, a gas carrier, an electrical wire, a monitoring cable, a viewing cable, and a data cable,
   wherein said medical conduit is associated with at least one of: an intravenous pump, an oxygen supplementation system, a continuous positive airway pressure system, a feeding tube, an umbilical artery catheter, a fluid transport device, a hemofiltration system, a hemodialysis system, a ventilation system, an air conditioning system, an air humidification system, an air heating system, and at least one medical monitoring device, and
   wherein said medical monitoring device is configured to measure one of: ambient air temperature, body temperature, air humidity, neonate respiration, neonate cardiac function, neonate blood oxygenation, neonate brain activity, neonate blood pressure, and neonate cardio-respiratory activity.

9. The neonatal care unit according to claim 1, further comprising one or more sensors configured to monitor at least one of, ambient air temperature, body temperature, air humidity, neonate respiration, neonate cardiac function, neonate blood oxygenation, neonate brain activity, neonate blood pressure, neonate cardio-respiratory activity.

10. The neonatal care unit of claim 9, further comprising a controller configured to control the provision of at least one of: a medication, heat, humidity, nutrition and ventilation, based on one or more signals received from the one or more sensors.

11. The neonatal care unit according to claim 1, further comprising a heating element.

12. The neonatal care unit according to claim 1, further comprising one or more straps configured to extend around said torso and operably connect using securing means.

13. The neonatal care unit according to claim 1, wherein the sealing skirt is included in a garment configured to be worn by the human.

14. The neonatal care unit according to claim 1, further comprising an infrared reflective coating applied to at least a portion of an interior surface of said hood.

15. The neonatal care unit of claim 14, wherein the infrared reflective coating is transparent in visible light.

16. The neonatal care unit according to claim 1, further comprising an infrared reflective cover configured to be positioned over said hood and cover an exterior surface of said hood, other than said at least one access opening, said at least two arm ports, and said at least one port.

17. A method of neonatal caring comprising:

providing a neonatal care unit comprising:
- a hood defining an interior space and having a bottom opening, wherein said hood is dimensioned to accommodate a neonate,
- a sealing skirt extending along at least a portion of a peripheral edge of said bottom opening and configured to engage at least part of a front torso region of a human in a sealing engagement,
- at least one access opening located about a sidewall of said hood and dimensioned to allow passage of said neonate therethrough,
- at least two arm ports located about said sidewall, wherein each arm port is dimensioned to allow passage of a hand therethrough, and
- at least one port configured to allow passage of a medical conduit therethrough;

positioning said neonatal care unit about a front torso region of a human, such that said sealing skirt engages at least part of said front torso region in a sealing engagement;

placing a neonate within said interior space, wherein said neonate is passed into said interior space through one of said at least one access opening; and passing at least one medical conduit through said at least one port.

18. The method of claim 17, further comprising:

monitoring at least one parameter of the neonate using at least one sensor included in the neonatal care unit, and controlling provision of at least one of: a medication, heat, humidity, nutrition and ventilation ports, based on the at least one parameter.

19. The method according to claim 17, further comprising providing exhale humidified air from the human to the hood via a mouthpiece included in the hood.

* * * * *